United States Patent [19]

Siren et al.

[11] Patent Number: 5,003,098

[45] Date of Patent: Mar. 26, 1991

[54] METHOD OF REDUCING OR ELIMINATING ADVERSE EFFECTS OF A PHARMACEUTICAL COMPOSITION OR A DRUG

[75] Inventors: Matti Siren, Lugano, Switzerland; David Blake, Worchestershire, United Kingdom

[73] Assignee: Perstorp AB, Sweden

[21] Appl. No.: 214,500

[22] Filed: Jul. 1, 1988

Related U.S. Application Data

[63] Continuation-in-part of Ser. No. 15,699, Feb. 17, 1987, which is a continuation-in-part of Ser. No. 788,829, Oct. 18, 1985, Pat. No. 4,777,134, and a continuation-in-part of Ser. No. 173,985, Mar. 23, 1988, which is a continuation-in-part of Ser. No. 38,230, Apr. 14, 1987, which is a continuation-in-part of Ser. No. 15,679, Feb. 17, 1987, Pat. No. 4,797,390.

[30] Foreign Application Priority Data

Oct. 23, 1984 [SE] Sweden .............................. 84052950

[51] Int. Cl.$^5$ .............................................. C07F 9/02
[52] U.S. Cl. ................................. 558/155; 514/103; 514/970
[58] Field of Search ................. 514/103, 970; 558/155

[56] References Cited

U.S. PATENT DOCUMENTS 2,723,938  11/1955  Buckwalter ........................ 514/103
3,591,665  7/1971  Kimura et al. ................ 252/400.2 X

OTHER PUBLICATIONS

Lim et al., Biochim. Biophys. Acta 302, 316–328 (1973).
Tomlinson et al., Biochemistry, 1, No. 1, 166–171 (1962).
Kerr et al., Arch of Biochem & Biophys, 96, 347–352 (1962).
Suematsu et al., Biochem. & Biophys. Res. Comm., 120, No. 2, 481–485 (1984).
Streb et al., Nature, 306, 67–68 (1983).
Irvine et al., Biochem J., 223, 237–243 (1984).

*Primary Examiner*—Werren B. Lone
*Assistant Examiner*—Margaret Argo
*Attorney, Agent, or Firm*—Scully, Scott, Murphy & Presser

[57] ABSTRACT

A method of reducing or eliminating adverse effects of a pharmaceutical composition or a drug is disclosed. The method comprises administering to an animal or a human an amount of at least one specific isomer of inositol triphosphate sufficient to reduce or eliminate said adverse effects.

7 Claims, No Drawings

METHOD OF REDUCING OR ELIMINATING ADVERSE EFFECTS OF A PHARMACEUTICAL COMPOSITION OR A DRUG

REFERENCE TO RELATED APPLICATIONS

This is a continuation-in-part of U.S. patent application, Ser. No. 015,699, filed Feb. 17, 1987, now U.S. patent application, Ser. No. 788,829, filed Oct. 18, 1985, now U.S. Pat. No. 4,777,134 issued Oct. 11, 1988. This is also a continuation-in part of U.S. patent application, Ser. No. 173,985, filed Mar. 28, 1988, U.S. patent application, Ser. No. 038,230 filed Apr. 14, 1987 U.S. patent application, Ser. No. 015,679, filed Feb. 17, 1987, now U.S. Pat. No. 4,797,390 issued Jan. 10, 1989.

FIELD OF INVENTION

The present invention relates to a method of reducing or eliminating adverse effects of a pharmaceutical composition or a drug on a human or an animal.

BACKGROUND TO THE INVENTION

Many pharmaceuticals, when administered to the body, causes, besides the beneficial effects, adverse effects, which at best is irritating to the treated patient but at worst leads to a damage that cannot be cured.

Several theories have been advanced to explain the mechanism by which substances such as drugs exert their negative side effects. The organs in the body and especially the cells are exposed to an environment where it is very essential that the levels of important constituents are balanced. Thus for the cell to work in a proper way the components of the cell membrane must be in correct order concerning for example lipid content, protein content, etc. In addition to this the signal transmission from extracellular mediators to intracellular events must have the possibilities to function properly.

An adverse disturbance of the function of an organ or a cell may be caused by a changed balance of minerals and metal ions. Many metals are necessary for the body, that is, they are essential for the proper function of proteins, such as enzymes and for signals mediating different metabolic properties. Furthermore metal ions are affecting the charge and pH of constituents of the cell membrane which are important for the function. However, in too high concentrations in certain parts of the body these metals can give harmful effects. This case is valid for instance for iron, copper, zinc, magnesium and calcium. In addition to this non-essential metals such as cadmium, lead and mercury, which are normally detoxified by certain proteins, can under certain circumstances be released to parts of the body where harmful effects may arise by interference with biologically important molecules.

An imbalance of e.g. iron or copper can in a medium of oxygen cause the formation of free radicals. These very reactive species can cause severe damages to cell membranes by so called lipid peroxidation. These processes disturb the normal activities of the cell.

SUMMARY OF THE INVENTION

According to the presetn invention it has qute unexpectedly been found possible to reduce or eliminate adverse effects caused by a pharmaceutical composition or drug, by administering to an animal or a human an amount of at least one specific isomer of inositol triphosphate ($IP_3$) sufficient to reduce or eliminate said adverse effects.

DETAILED DESCRIPTION OF THE PREFERRED EMBODIMENTS

The use of an amount of at least one specific isomer of inositol triphosphate for reduction or eliminating adverse side effects caused by a pharmaceutical composition or drug is especially useful when the adverse effects depend on an imbalance in the metal or metal ion status and/or a changed formation of free radicals.

The method of the present invention reduces or eliminates adverse effects, for example damages to the intestine and colon, damages to the cardiovascular system, damage to the central nervous system, damage to the lungs, the cell membrane and to the eye, caused by a pharmaceutical composition or drug.

The present invention also concerns a method of reducing or eliminating adverse effects caused by a pharmaceutical composition or drug at the treatment of for example iron overload, inflammations, tumours or malaria or diseases in the central nervous system. Specific pharmaceutical compositions or drugs are e.g. certain antimicrobials, antivirals, antifungals, antibacterials and antibiotics.

However, the present invention comprises a reduction or elimination of adverse effects in any part of the body by administering thereto at least one specific isomer of inositol triphosphate, where said adverse effect is connected to a pharmaceutical composition or drug used for treatment of any disease where the adverse effect is caused by a disturbed metal balance and/or the changed formation of free radicals in the body.

The pharmaceutical composition or drug causing the adverse effect and the isomer of inositol triphosphate can be administered separately or jointly.

The $IP_3$ isomer or isomers, which accomplish the above objectives and which are used according to the invention can, for example, be produced by:

(1) Enzymatic breakdown starting from $IP_4$, $IP_5$ and-/or $IP_6$.
(2) Chemical hydrolysis starting from $IP_4$, $IP_5$ and/or $IP_6$.
(3) Chemical synthesis starting, for example, with inositol, $IP_1$, $IP_2$ and phosphate.
(4) Enzymatic synthesis starting for example from inositol, $IP_1$, $IP_2$ and phosphate.
(5) Microbiological production (including also hybrid DNA-techniques).
(6) Chemical or enzymatic migration of inositol phosphate or
(7) Chemical or enzamatic hydrolysis of substituted inositol phosphate.

A combination of two or more of the above mentioned procedures may also be used.

It is suitable that the $IP_3$ isomer or isomers according to the invention are used in unit dosage form. Tablets, granulates or capsules are suitable administration forms for such unit dosage. Furthermore, tablets and granulates can easily be surface treated such as to provide an enteric coating to prevent an uncontrolled hydrolysis in the stomach and to bring about a desired absorption in the intestine. Other suitable administration forms are slow release and transdermal administration. A usual pharmaceutically acceptable additive, excipient and/or carrier can be included in the dosage form. The tablets or granulates can also contain a disintegrant which causes the tablets or the granulates, respectively, to disintegrate easily in the intestine. In certain cases, especially in acute situations, it is preferable to use the unit dosage in the form of a solution for intravenous administration.

One or more specific IP$_3$ isomers disclosed hereinafter, each present in substantially pure form are preferred. Thus, the different isomers can be isolated from each other in substantially pure form, which means that they have a purity of 80–100%, such as 82–100% or 85–100%, preferably 90–100%. Since the isomers can be produced in pure form they can be mixed in any proportion, of course.

The production of IP$_3$ and the isolation of the different isomers thereof are disclosed for instance in the U.S. patent application Ser. No. 788,829 filed on Oct. 18, 1985 and the equivalent U.K. Patent application Ser. No. 2,169,602 and the U.S. patent application Ser. No. 015,699 filed on Feb. 17, 1987.

It is in most cases suitable that the IP$_3$-isomer or isomers which are used according to the invention are present in salt form. The salt should preferably consist of a sodium, calcium, zinc or magnesium salt or a mixture of two or more of these salts. Calcium and zinc salts or mixtures of these are especially preferred.

For administration to human patients appropriate dosages can routinely be determined by those skilled in this art by extension of the results obtained in animals at various dosages. The preferred dosage for humans falls within the range of 0.1 to 100, especially 0.1–50 mg IP$_3$/day/kg body weight.

In animal experiments, no toxic effects were seen after administration of very high doses of IP$_3$, 160 mg/kg body weight by intravenous injection to mice or 1600 mg/kg body weight by intraperitoneal injection to mice.

The IP$_3$ isomer used according to the present invention is preferably

D-myo-inositol-1,2,6-triphosphate of the formula

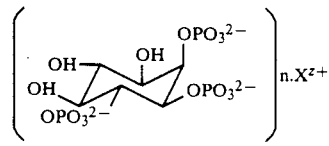

where X is hydrogen, at least one univalent, divalent or multivalent cation, or a mixture thereof, n is the number of ions, and z is the charge of the respectively ion;

D-myo-inositol-1,2,5-triphosphate of the formula

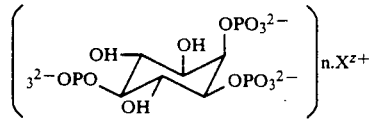

where X, n and z have the above mentioned meaning;
myo-inositol-1,2,3-triphosphate of the formula

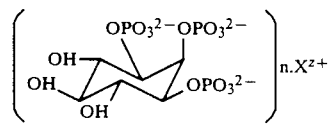

where X, n and z have the above mentioned meaning;
L-myo-inositol-1,3,4-triphosphate of the formula

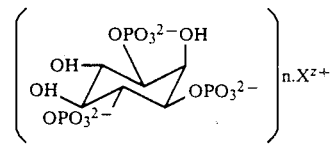

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of above isomers D-myo-inositol-1,2,6-triphosphate if preferred.

Other inositol triphosphate isomers that may be utilized in the present invention have the structural formula

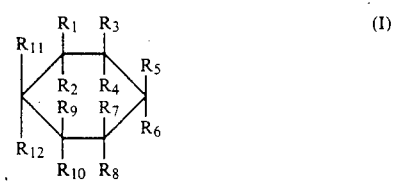

One group of inositol triphosphate compounds is defined by structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen. Another group of inositol triphosphates is defined by structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol triphosphates is defined by structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol triphosphates is defined by structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group ore inositol triphosphates is defined by structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol triphosphates is defined by structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet another group of inositol triphosphates is defined by structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol triphosphates is defined by structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol triphosphate compounds within the contemplation of the above formula include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$, and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$, and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$, 1 and $R_{11}$ are hydroxyl and $R_2$, $R_4$, $R_6$, $R_8$, $R_9$ and $R_{12}$ are hydrogen;

$R_3$, $R_{10}$ and $R_{11}$, are phosphate, $R_1$, $R_5$, and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$, and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen; $R_1$, $R_3$ and $R_5$, are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$, and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$, and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$, and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$, and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$, are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$, are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$, and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$, and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$, and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$, and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$, 1 and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$, and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$, and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$, 1 and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$, and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$, are hydroxyl and $R_2$, $R_4$, $R_6$, $R_7$, $R_{10}$ and $R_{11}$ are hydrogen.

The above formula describes specific isomers of inositol triphosphate where the inositol is selected from the group myoinositol, cisinositol, epiinositol, alloinositol, neoinositol, mucoinositol, chiroinositol and scylloinositol.

The invention is further explained below in connection with embodiment examples of which example 1 shows the distribution effects of $IP_3$ on the cadmium content in different organs. Example 2 discloses the ability of $IP_3$ to scavenge toxic free radicals. Example 3 relates to the fact that, when the balance of certain metals are disturbed, an increased damage to the cell membrane can be observed. This damage is counteracted by the presence of $IP_3$. Example 4 teaches the elimination of adverse effects of a pharmaceutical composition in the presence of $IP_3$. Examples 5, 6, 8, 9 and 10 relate to the production of $IP_3$ and examples 11 and 12 describe the manufacture of a solution for injection and tablets of $IP_3$ respectively.

It should be understood that the invention is not limited to the specific details of these examples.

EXAMPLE 1

Mice weighing 18–20 gram at the start of the experiment were used. During the experiment and for at least seven days before the experiment the mice were fed a semisynthetic diet free of inositol phosphates. The mice were divided in two groups.

They received daily intraperitoneal injections of physiological saline or D-myo-inositol-1,2,6-triphosphate (IP$_3$) for 9 days. The dose of IP$_3$ was $10^{-6}$ mol/-day and the injected volume was 0.2 ml.

On day two of the experiment, 5-10 minutes after the second intraperitoneal injection, all mice received an intravenous injection of 2.5 microcurie of $^{109}$Cd as cadmium chloride in 50 ul of saline. After the last intraperitoneal injection the mice were killed and several organs were dissected out and weighed.

Radioactivity in the different organs was measured by counting with a gamma-counter. Radioactivity in the organs of the IP$_3$-treated animals was compared with that of control animals, which had been treated with saline for the same period of time. In the results radioactivity in the organs of the animals treated with IP$_3$ is expressed as % of the radioactivity found in controls. The results were as follows:

| Organ | Cd-level compared to control (%) |
| --- | --- |
| Lung | 74 |
| Heart | 67 |
| Aorta | 65 |
| Spleen | 57 |
| Salivary gland | 87 |
| Liver | 100 |
| Kidney | 104 |

The results show the preventive effect of IP$_3$ when sensitive organs, such as lung, heart, aorta and spleen are exposed to heavy metals such as cadmium.

EXAMPLE 2

Reaction mixtures with the following compositions were incubated for 5 minutes at 37° C.:

| | |
| --- | --- |
| KH$_2$PO$_4$ buffer pH 7.4 | 20 mM |
| EDTA | 0.1 mM |
| Salicylate | 1 mM |
| Ascorbate | 1 mM |
| H$_2$O$_2$ | 3.3 mM |
| Fe$^{3+}$ | 0.05 mM |
| IP$_3$ | 0, 2.5, 5 or 10 mM |

The products formed by oxidation of salicylate were quantified with HPLC. The IP$_3$ was D-myo-inositol-1,2,6-triphosphate.

The system studies radical scavening. Under these reaction conditions, all Fe$^{3+}$ will form complex with EDTA. The Fe-EDTA complex will induce free-radical formation, and the ability of IP$_3$ to prevent oxidation of salicylate is studied.

The results of the experiment were:

| Concentration of IP$_3$, mM | Relative amount of salicylate oxidized |
| --- | --- |
| 0 | 100 |
| 2.5 | 44 |
| 5 | 43 |
| 10 | 19 |

Thus, IP$_3$ is able to act as a free-radical scavenger, thereby preventing free-radical induced damage to other molecules or tissues.

EXAMPLE 3

The structure of the cell membrane is very essential for the proper function of the cell. It is known that the presence of Fe(II) in liposomes (phospholipids from oxbrain) damages the cell membrane. One measure of the damage is the determination of the lipidperoxides formed when the metal is added to the preparation.

In this example, the synergistic damaging effects of the cell membrane when Pb, Ni, Cr, Al or Cd is added to the preparations together with Fe(II), were investigated. Furthermore the preventive effect of the presence of D-myo-inositol-1,2,6-triphosphate (IP$_3$) was evaluated.

| Reaction mixture | |
| --- | --- |
| Clark-Lubs buffer pH 5.5 | 40 mM |
| Liposomes, Sigma type VII | 1 mg/ml |
| IP$_3$ | 1.0 mM |
| (NH$_4$)$_2$Fe(So$_4$)$_2$ | 0.1 mM |
| Pb$^{2+}$, Ni$^{2+}$, Cr$^{3+}$, Al$^{3+}$, Cd$^{2+}$ respectively | 0.4 mM |

The reaction mixture (1.0 ml) was incubated for 2 hours at 37° C. After incubation 0.5 ml of thiobarbituric acid and 0.5 ml 25% HCl were added and the mixture was heated at 100° C. for 20 minutes. The amount of lipid peroxides was measured by measuring the absorbance at 532 nm.

| Experiment | Fe | Pb | Ni | Cr | Al | Cd | IP$_3$ | Absorbance |
| --- | --- | --- | --- | --- | --- | --- | --- | --- |
| 1 | — | — | — | — | — | — | — | 0.044 |
| 2 | 0.1 | — | — | — | — | — | — | 0.47 |
| 3 | 0.1 | — | — | — | — | — | 1.0 | 0.25 |
| 4 | 0.1 | 0.4 | — | — | — | — | — | 0.54 |
| 5 | 0.1 | 0.4 | — | — | — | — | 1.0 | 0.37 |
| 6 | 0.1 | — | 0.4 | — | — | — | — | 0.76 |
| 7 | 0.1 | — | 0.4 | — | — | — | 1.0 | 0.34 |
| 8 | 0.1 | — | — | 0.4 | — | — | — | 0.57 |
| 9 | 0.1 | — | — | 0.4 | — | — | 1.0 | 0.26 |
| 10 | 0.1 | — | — | — | 0.4 | — | — | 0.39 |
| 11 | 0.1 | — | — | — | 0.4 | — | 1.0 | 0.16 |
| 12 | 0.1 | — | — | — | — | 0.4 | — | 0.22 |
| 13 | 0.1 | — | — | — | — | 0.4 | 1.0 | 0.13 |

The structural change of the cell membranes caused by Fe(II) (Experiment 2) was strongly increased by the presence of Pb (Experiment 4), Ni (Experiment 6), Cr (Experiment 8), Al (Experiment 10) or Cd (Experiment 12). These effects were counteracted by IP$_3$ (Experiments 5, 7, 9, 11 and 13).

A disfunction of the cell caused by disturbance in the structure of the cell membrane can be linked to adverse effects caused by distribution of many pharmaceutical compositions or drugs.

EXAMPLE 4

The pharmaceutical composition desferrioxamine is used for treating patients with iron-overload. The treatment causes severe adverse effects to the retina of the eye for instance.

This defect in the retina can be measured in animal experiments and shown in an electroretinogram. 16 male rats, weighing approx. 300 g, were divided into four groups:

Group A were injected subcutaneously with 150 mg of D-myo-inositol-1,2,6-triphosphate (IP$_{33}$) dissolved in 0.5 ml saline, pH 6.8.

Group B received 150 mg IP$_3$ and 150 mg desferrioxamine subcutaneously.

Group C received 150 mg desferrioxamine only.

Group D received only saline and acted as a control.

Electroretinograms were recorded on all groups at different time intervals by the following method:

The pupil of each animal were dilated and a reference electrode was inserted under the skin behind the orbit. An earth electrode was placed subcutaneously between the ears and the measurement was performed with a titanium electrode which was placed lightly on the corneal surface.

The condition of the retina was measured as a function of time where the value 100 is the lower normal limit. The results are shown in the following table:

|  | Day | | | | | |
|---|---|---|---|---|---|---|
|  | 0 | 2 | 5 | 9 | 12 | 15 |
| Group A | 125 | 128 | 119 | 121 | 123 | 125 |
| Group B | 125 | 129 | 125 | 121 | 125 | 125 |
| Group C | 125 | 53 | 50 | 70 | 85 | 125 |
| Group D | 125 | 128 | 122 | 120 | 120 | 125 |

As can be seen the value for Group D (the control) and Group A (only IP$_3$) is well above the lower normal limit. Group C (only desferrioxamine) is very negatively affecting the retina while the presence of IP$_3$ in Group B (desferrioxamine and IP$_3$) totally abolish these effects.

Thus the presence of IP$_3$ eliminates the adverse effects of desferrioxamine.

EXAMPLE 5

Hydrolysis of sodium phytate with baker's yeast and fractionation of a mixture of inositol phosphates.

A 0.7 gram quantity of sodium phytate (from corn, Sigma Chemical Co) was dissolved in 600 ml sodium acetate buffer pH 4.6. 50 gram of baker's yeast from Jastbolaget, Sweden (dry substance: 28%, nitrogen content: 2%, phosphorus content: 0.4%) was added with stirring and incubation was continued at 45° C. The dephosphorylation was followed by determining the inorganic phosphorus released. After 7 hours when 50% inorganic phosphorus was liberated the hydrolysis was stopped by adding 30 ml of ammonia to pH 12. The suspension was centrifuged and the supernatant was collected.

400 ml of the supernatant was passed through an ion-exchange column (Dowex 1, chloride form, 25 mm×250 mm) and eluted with a linear gradient of hydrochloric acid (0–0.7 N HCl).

Aliquots of eluted fraction's were completely hydrolyzed in order to determine the contents of phosphorus and inositol. The peaks correspond to different inositol phosphates i.e. a peak with the ratio of phosphorus to nositol of three to one consists of inositol triphosphates etc.

EXAMPLE 6

Structural determination of isomers of inositol triphosphate.

The fraction obtained in example 5 with a phosphorus/inositol ratio of three to one was neutralized and evaporated before analysis with H-NMR. Data show that the peak consists of myo-inositol-1,2,6-triphosphate.

EXAMPLE 7

A 0.5 gram quantity of D-chiro-inositol was dissolved in 1 ml phosphoric acid at 60° C. 20 g polyphosphoric acid was added and the mixture was heated to 150° C. under vacuum for 6 hours. The mixture was diluted with water to a volume of 200 ml and passed through an ion-exchange column (Dowex 1, chloride form, 25 mm×250 mm) and eluted with a linear gradient of hydrochloric acid (0–2.0 N HCl).

The content of the peak with the ratio of phosphorus to inositol of six to one was precipitated by addition of calcium hydroxide. The precipitate was filtered, washed and mixed with 10 ml of a cation-exchange resin to give the acid form of the inositolhexaphosphate. After neutralization with sodium hydroxide and freeze-drying the sodium salt of D-chiro-inositolhexaphosphate was obtained.

EXAMPLE 8

A 0.8 gram quantity of epi-inositol was dissolved in 1.5 ml of phosphoric acid at 60° C. 32 g polyphosphoric acid was added and the mixture was heated to 150° C. under vacuum for 6 hours. The mixture was diluted with water to a volume of 200 ml and passed through an ion-exchange column (Dowex, chloride form, 25 mm×250 mm) and eluted with a linear gradient of hydrochloric acid (0–2.0 N HCl).

The content of the peak with the ratio of phosphorus to inositol of six to one was precipitated by addition of calcium hydroxide. The precipitate was filtered, washed and mixed with 10 ml of a cation-exchange resin to give the acid form of the inositolhexaphosphate. After neutralization with sodium hydroxide and freeze-drying the sodium salt of epi-inositolhexaphosphate was obtained.

EXAMPLE 9.

A 0.8 gram quantity of the sodium salt of D-chiro-inositolhexaphosphate produced according to Example 7 was dissolved in 300 ml sodium acetate buffer, pH 5.2. 1.3 gram wheat phytase (EC 3.1.3.26, 0.015 U/mg from Sigma Chemical Co.) was added and the mixture was incubated at 38° C.

After the liberation of 50% inorganic phosphorus the hydrolysis was stopped by adding ammonia to pH 12.

The mixture containing D-chiro-nositolphosphates was passed through an ion-exchange column (Dowex 1 chloride form, 25 mm×250 mm) and eluted with a linear gradient of hydrochloric acid (0–0.7 N HCl).

The peak with the ratio of phosphorus to inositol of three to one was neutralized with 1.0 M sodium hydroxide and freeze-dried.

Structural determination with NMR and IR showed the product to be D-chiro-inositoltriphosphate.

EXAMPLE 10

A 1.2 gram quantity of the sodium salt of epi-inositolhexaphosphate produced according to Example 8 was dissolved in 500 ml sodium acetate buffer, pH 5.2. 2.0 gram wheat phytase (EC 3.1.3.26, 0.015 U/mg from Sigma Chemical Co.) was incubated at 38° C.

After the liberation of 50% inorganic phosphorus the hydrolysis was stopped by adding ammonia to pH 12.

The mixture containing epi-inositolphosphates was passed through an ion-exchange column (Dowex 1, chloride form, 25 mm×250 mm) and eluted with a linear gradient of hydrochloric acid (0–0.7 N HCl).

The peak with the ratio of phosphorus to inositol of three to one was neutralized with 1.0 M sodium hydroxide and freeze-dried.

Structural determination with NMR and IR showed the product to be epi-inositoltriphosphate.

EXAMPLE 11

Solution of potassium salt of D-myo-inositol-1,2,6-triphosphate for injection.

0.5 g of the potassium salt of $IP_3$ and 0.77 g NaCl were dissolved in 98.73 ml of water for injection to form a solution suitable for injection into a person or an animal.

EXAMPLE 12

Tablets of calcium salt of D-myo-inositol-1,2,6-triphosphate.

Tablets of the calcium salt of D-myo-inositol-1,2,6-triphosphate were produced in the following way. 50 g calcium salt of D-myo-inositol-1,2,6-triphosphate, 132 g lactose and 6 g acacia were mixed. Purified water was then added to the mixture, whereupon the mixing was continued until a suitable consistency was obtained. The mixture was sieved and dried. Then the mixture was blended with 10 g talcum and 2 g magnesium stearate. The mixture was compressed into tablets each weighing 200 mg.

I claim:

1. A method of reducing or eliminating adverse effects of a pharmaceutical composition or a drug comprising administering to an animal or a human who has suffered adverse effects of a pharmaceutical composition or a drug, an amount of at least one specific isomer selected from the group consisting of D-myo-inositol-1,2,6-triphosphate, myo-inositol-1,2,3-triphosphate and L-myo-inositol-1,3,4-triphosphate sufficient to reduce or eliminate said adverse effects.

2. A method according to claim 1, wherein the adverse effects depend on a disturbed metal balance in the body.

3. A method according to claim 1, wherein the adverse effects depend on free radical formation in the body.

4. A method according to claim 1, wherein the pharmaceutical composition or drug and the isomer of inositol triphosphate are administered separately.

5. A method according to claim 1, wherein the pharmaceutical composition or drug is used against iron overload.

6. A method according to claim 1, wherein the adverse effect caused by the pharmaceutical composition or drug is damage to the eye.

7. A method according to claim 1, wherein the adverse effect caused by the pharmaceutical composition or drug is damage to the cell membrane.

* * * * *

UNITED STATES PATENT AND TRADEMARK OFFICE
CERTIFICATE OF CORRECTION

PATENT NO. : 5,003,098
DATED : March 26, 1991
INVENTOR(S) : Matti Siren

It is certified that error appears in the above-identified patent and that said Letters Patent is hereby corrected as shown below:

Column 1, line 64: "presetn" should read as --present--

Column 2, line 52: "enzamatic" should read as --enzymatic--

Column 4, line 48: "ore" should read as --of--

Column 5, line 16: "$R_5$ 1 and $R_{11}$" should read as --$R_5$ and $R_{11}$--

Column 6, line 16: "$R_5$, 1 and" should read as --$R_5$ and--

Column 6, line 31: "$R_5$, 1 and" should read as --$R_5$ and--

Column 8, line 48: "disturbance" should read as --disturbances--

Column 8, line 63: "($IP_{33}$)" should read as --($IP_3$)--

Column 9, line 52: "nositol" should read as --inositol--

UNITED STATES PATENT AND TRADEMARK OFFICE
CERTIFICATE OF CORRECTION

PATENT NO. : 5,003,098

DATED : March 26, 1991

INVENTOR(S) : Matti Siren

It is certified that error appears in the above-identified patent and that said Letters Patent is hereby corrected as shown below:

Column 10, line 42: "D-chiro-nositolphosphates" should read as --D-chiro-inositolphosphates--.

Signed and Sealed this

Eighth Day of September, 1992

Attest:

DOUGLAS B. COMER

*Attesting Officer*  *Acting Commissioner of Patents and Trademarks*